United States Patent
Barber et al.

(10) Patent No.: US 10,267,904 B2
(45) Date of Patent: Apr. 23, 2019

(54) ARTIFICIAL SKIN AND HUMAN PHANTOM FOR USE IN ACTIVE MILLIMETER WAVE IMAGING SYSTEMS

(71) Applicant: The United States of America, as represented by the Secretary of Homeland Security, Washington, DC (US)

(72) Inventors: Jeffrey Brian Barber, Vineland, NJ (US); Peter Roland Smith, Westfield, NJ (US); James Christopher Weatherall, Atlantic City, NJ (US); Barry Thomas Smith, Egg Harbor City, NJ (US)

(73) Assignee: The United States of America, as represented by the Secretary of Homeland Security, Washington, DC (US)

( * ) Notice: Subject to any disclaimer, the term of this patent is extended or adjusted under 35 U.S.C. 154(b) by 0 days.

(21) Appl. No.: 16/058,522

(22) Filed: Aug. 8, 2018

(65) Prior Publication Data
US 2019/0060526 A1 Feb. 28, 2019

Related U.S. Application Data

(63) Continuation-in-part of application No. 16/058,053, filed on Aug. 8, 2018.
(Continued)

(51) Int. Cl.
G01S 7/497 (2006.01)
G01S 13/89 (2006.01)
(Continued)

(52) U.S. Cl.
CPC .......... *G01S 7/497* (2013.01); *G01J 5/522* (2013.01); *G01S 7/52004* (2013.01); *G01S 13/89* (2013.01); *G01J 2005/0077* (2013.01)

(58) Field of Classification Search
CPC ..... G01J 5/522; G01J 1/42; G01J 4/04; G01S 1/022; G01S 3/023; G01S 3/7803; G01S 5/021; G01S 7/497; G01S 7/52004
(Continued)

(56) References Cited

U.S. PATENT DOCUMENTS 4,621,265 A * 11/1986 Buse ............... F41G 7/003
250/252.1
5,886,534 A * 3/1999 Bakhtiari ............ G01N 22/02
324/642

(Continued)

OTHER PUBLICATIONS

Barber, Jeffrey, et al., "Developing an ANSI standard for image quality tools for the testing of active millimeter wave imaging systems", Proceedings of SPIE vol. 10189, 1018905, May 11, 2017.
(Continued)

*Primary Examiner* — Taeho Jo
(74) *Attorney, Agent, or Firm* — Lavanya Ratnam; Trenton Roche; William Washington

(57) ABSTRACT

The present disclosure is directed to an artificial skin including: a radar absorbing layer; a conductive layer comprising at least one material selected from the group consisting of a semiconductive oxide deposited onto a substrate and an electrically conductive polymer, wherein the substrate is in contact with the radar absorbing layer, and wherein the artificial skin has a reflection coefficient substantially equal to a human skin reflection coefficient, the human skin reflection coefficient being determined at an electromagnetic radiation frequency ranging from 1-500 GHz. A human phantom composed of the artificial skin and methods of using the human phantom are also disclosed.

21 Claims, 2 Drawing Sheets

Related U.S. Application Data

(60) Provisional application No. 62/542,596, filed on Aug. 8, 2017.

(51) Int. Cl.
*G01S 7/52* (2006.01)
*G01J 5/52* (2006.01)
*G01J 5/00* (2006.01)

(58) Field of Classification Search
USPC ...................................................... 250/252.1
See application file for complete search history.

(56) References Cited

U.S. PATENT DOCUMENTS

| | | | |
|---|---|---|---|
| 9,075,132 B2 | 7/2015 | Barber et al. | |
| 2002/0173068 A1* | 11/2002 | Kido | C23C 14/352 438/99 |
| 2007/0296624 A1* | 12/2007 | Katano | H01Q 17/00 342/1 |
| 2012/0256777 A1* | 10/2012 | Smith | G01S 7/412 342/22 |
| 2014/0014829 A1* | 1/2014 | Barber | G01S 7/40 250/252.1 |
| 2015/0109655 A1* | 4/2015 | Vigneron | G02B 1/005 359/290 |
| 2015/0275385 A1* | 10/2015 | Chandrasekhar | G02F 1/1506 205/50 |
| 2016/0131756 A1* | 5/2016 | Einat | G01S 13/887 342/27 |
| 2016/0245705 A1* | 8/2016 | Weatherall | G01J 5/522 |
| 2017/0184936 A1* | 6/2017 | Chandrasekhar | G02F 1/1506 |
| 2017/0356941 A1* | 12/2017 | Ahmed | G01N 23/06 |

OTHER PUBLICATIONS

Smith, Peter R., et al., "Measurements of the dielectric properties of explosives and inert materials at millimeter wave frequenciess (V-band and above) using free space reflection methods", Proceedings of SPIE Vo. 10189, 1018908, May 11, 2017.

Pierre Désaulniers and Simon Thibault, Performance evaluation of panoramic electro-optic imagers using the TOD method, Proceedings of SPIE—The International Society for Optical Engineering, vol. 8014, 801409, May 2011.

Derraik, José G. B. et al., "Effects of Age, Gender, BMI, and Anatomical Site on Skin Thickness in Children and Adults with Diabetes", PLOS ONE, vol. 9, Issue 1, e86637, Jan. 21, 2014.

\* cited by examiner

ARTIFICIAL SKIN AND HUMAN PHANTOM FOR USE IN ACTIVE MILLIMETER WAVE IMAGING SYSTEMS

CROSS REFERENCE TO RELATED APPLICATIONS

This application is a Continuation-in-Part (CIP) of U.S. application Ser. No. 16/058,053, filed 8 Aug. 2018, which claims the benefit of priority of U.S. Provisional Application No. 62/542,596, filed 8 Aug. 2017. The contents of these applications are herein incorporated by reference in their entirety.

GOVERNMENT RIGHTS

This invention was made with government support under Contract Nos. HSHQDC-15-J-00395 and HSHQDC-13-A-00023 awarded by the U.S. Department of Homeland Security. The United States Government has certain rights in this invention.

BACKGROUND

The "background" description provided herein is for the purpose of generally presenting the context of the disclosure. Work of the presently named inventor, to the extent it is described in this background section, as well as aspects of the description, which may not otherwise qualify as prior art at the time of filing, are neither expressly nor impliedly admitted as prior art against the present disclosure.

Active millimeter wave imaging systems are being used at checkpoints for screening humans for security reasons. These systems illuminate a human target with millimeter wave radiation, generally in a range from 1-500 GHz, and collect signals reflected off a body. These signals are used to generate an image of a human target for the purposes of detecting threat objects, such as guns, knives, explosives, drugs, etc.

Generally millimeter wave images are contrast (grayscale) images. In order to ensure that an active millimeter wave imaging system is able to accurately detect a threat object, it is helpful to determine whether or not the imaging system can resolve differences in grayscale between a variety of human targets and an object of interest.

SUMMARY

Given that different human targets of different body mass indices may reflect differing amounts of signal after illumination with an active millimeter wave imaging system, the present inventors developed an artificial skin and a human phantom, which may be configured to produce reflection coefficients substantially equal to that of human targets at normal, overweight and/or obese body mass indices at millimeter wave frequencies. The artificial skin and human phantoms of the present disclosure may be used to assess how well a given active millimeter wave imaging system can resolve differences between human subjects at varying body mass indices and a specific threat object.

In one aspect, the present disclosure is directed to an artificial skin including: a radar absorbing layer; a conductive layer comprising at least one electrically conductive material selected from the group consisting of a semiconductive oxide deposited onto a substrate and an electrically conductive polymer, wherein the substrate is in contact with the radar absorbing layer, and wherein the artificial skin has a reflection coefficient substantially equal to a human skin reflection coefficient, the human skin reflection coefficient being determined at an electromagnetic radiation frequency ranging from 1-500 GHz.

In another aspect, the present disclosure is directed to a human phantom including a surface comprising a radar absorbing layer; and a conductive layer including an electrically conductive material selected from the group consisting of a semiconductive oxide deposited onto a substrate and an electrically conductive polymer, wherein the substrate is in contact with the radar absorbing layer, and wherein the conductive layer has a reflection coefficient substantially equal to a human skin reflection coefficient, the human skin reflection coefficient being determined at an electromagnetic radiation frequency in a range from 1-500 GHz.

The present disclosure is also directed to a method of testing a contrast resolution sufficiency of an active millimeter wave imaging system including: imaging a human phantom including a threat object with an active millimeter wave imaging system, wherein the human phantom includes: a surface comprising a radar absorbing layer; a conductive layer including an electrically conductive material deposited onto a substrate, wherein the substrate is in contact with the surface that includes the radar absorbing layer, and wherein the electrically conductive material is selected from the group consisting of a semiconductive oxide and an electrically conductive polymer, and wherein the conductive layer has a reflection coefficient substantially equal to a reflection coefficient of human skin, the reflection coefficient of human skin being determined at an electromagnetic radiation frequency ranging from 1-500 GHz, and determining a presence or absence of contrast resolution between the human phantom and the threat object, thereby testing the contrast resolution sufficiency of the active millimeter wave imaging system.

BRIEF DESCRIPTION OF THE DRAWINGS

An appreciation of the disclosure and many of the attendant advantages thereof may be understood by reference to the accompanying drawings. Included in the drawings are the following figures.

DETAILED DESCRIPTION

Artificial Skin

In one aspect, the present disclosure is directed to an artificial skin. As described herein, the artificial skin of the present disclosure may be used, for example, to assess an active millimeter wave system to determine whether the system is capable of distinguishing between a human skin of interest at a predetermined electromagnetic frequency, e.g., a human skin of a particular thickness at a predetermined frequency, and a threat object, such as a gun, a knife, an explosive or a drug.

As used herein an "active millimeter wave imaging system" refers to an imaging device or system that directs electromagnetic energy at, for example, a body, object or sample and then constructs an image based upon the energy reflected back from the body, object or sample. Generally, the formed images are contrast (grayscale) images.

Figure 1:
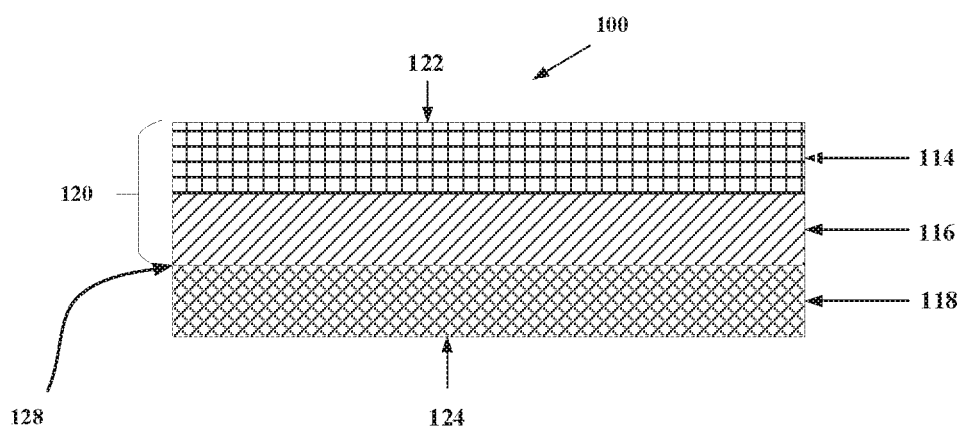
FIG. 1 depicts an implementation of an artificial skin of the present disclosure as described in the detailed description.

FIG. 1 provides an implementation of an artificial skin 100 including a conductive layer 120 and a radar absorbing layer 118. The conductive layer 120 comprises an electrically conductive material 114 and a substrate 116. The artificial skin 100 further includes an inner layer 124 and an outer layer 122. The conductive layer 120 also includes an inner layer 128. The artificial skin 100 is typically illuminated at outer layer 122 and reflects electromagnetic radiation, such as from an active millimeter wave system, at a level approximate to that of an electromagnetic response of human skin exposed to the electromagnetic radiation. In some embodiments, the artificial skin 100 has a reflection coefficient substantially equal to that of a human skin, the reflection coefficient of the human skin being determined at an electromagnetic radiation frequency in a range from 1-500 GHz.

One skilled in the art will appreciate that, after illumination with electromagnetic energy, the degree to which a human skin will reflect this energy can vary depending upon, for example, the thickness of the skin and the water content (e.g., blood vessels) of the skin. Generally, thinner skin exhibits a higher reflection coefficient than thicker skin. In addition, thinner skin typically has blood vessels closer to the skin surface, which also increases the ability of thinner skin to reflect electromagnetic energy at higher levels in comparison to that of thicker skin.

Human skin becomes thicker with increasing body mass index (BMI) for both genders at any age. See, for example, Derraik et al., "Effects of age, gender, BMI, and anatomical site on skin thickness in children and adults with diabetes," *PLoS ONE*, 2014, 9, e86637, doi: 10.1109/TGRS.2002.807006, which is herein incorporated by reference in its entirety.

As used herein, a "normal BMI" is a BMI ranging from 18.5-24.9 kg/m$^2$. As used herein, an "overweight BMI" is a BMI ranging from about 25.0-29.9 kg/m$^2$. As also used herein, an "obese BMI" is a BMI greater than 30 kg/m$^2$.

In some embodiments, the human skin in accordance with the present disclosure has a thickness comparable to a human subject with a normal BMI. In other embodiments, the human skin in accordance with the present disclosure has a thickness comparable to a human subject with an overweight BMI. In still other embodiments, the human skin in accordance with the present disclosure has a thickness comparable to a human subject with an obese BMI. The reflection coefficient of a human skin in accordance with the present disclosure at a particular BMI at a predetermined frequency may be determined, for example, by scanning the skin of a person at a desired BMI with an active millimeter wave system or from the scientific literature.

The reflection coefficient of artificial skin 100 can be tuned to attain a reflection coefficient substantially equal to that of a human skin type of interest, e.g., a BMI of interest at a predetermined frequency, by adjusting the type of electrically conductive material 114 used in the artificial skin 100 as described herein. As used herein "substantially equal" means that the artificial skin 100 has a reflection coefficient that is at least within about three standard deviations, such as at least within two standard deviations, of the reflection coefficient value of a human skin of a desired type, e.g., a desired BMI at a predetermined frequency.

The response of materials to electromagnetic radiation may be understood in reference to Jackson's "*Classical Electrodynamics*", which provides a detailed derivation of Maxwell's equations with respect to plane wave propagation in dielectric media. See Jackson, John D. *Classical Electrodynamics* p 341. John Wiley & Sons, Inc., 1999. Print., which is herein incorporated by reference in its entirety. Briefly, the propagation of electromagnetic radiation is a function of the complex dielectric constant for non-magnetic materials. Using Ohm's Law, the complex dielectric constant consists of a "normal" dielectric constant $\epsilon=n^2$ and a conductivity term $i\sigma/\omega$ where n is the index of refraction, $\sigma$ is the conductivity of the material and $\omega$ is the angular frequency of the radiation. Accordingly, by modulating the conductivity/resistance of a material, the reflection coefficient of that material can vary from near zero to unity. Accordingly, electrically conductive material 114 can be configured as herein described to exhibit a reflection coefficient that is substantially equal to a reflection coefficient of a human skin of interest at a predetermined frequency.

In some embodiments, the electrically conductive material 114 has a reflection coefficient that is independent of electromagnetic frequency in a particular frequency range, e.g., 1 to 500 GHz. Accordingly, in these embodiments, the reflection coefficient of artificial skin 100 remains constant across active millimeter wave systems, which may utilize different frequency ranges.

While artificial skin 100 may be configured to have a reflection coefficient that approximates the reflection coefficient of a human skin of interest, it is appreciated that human skin will produce a different reflection coefficient depending on the frequency of the electromagnetic radiation used for illumination. In some instances, artificial skin 100 is configured to have a reflection coefficient that approximately resembles that of a human skin of interest exposed to electromagnetic radiation having a frequency in the range of 1 to 500 GHz, such as 1 to 150 GHz, such as 70 GHz to 150 GHz, such as 60 GHz to 90 GHz, such as 18 GHz to 40 GHz. If the artificial skin 100 is designed to approximate a reflection coefficient of a human skin of interest exposed to electromagnetic radiation at a specific frequency e.g., 40 GHz, one skilled in the art will appreciate that changing the frequency of the electromagnetic radiation is likely to impact the ability of the artificial skin 100 to approximate the reflection coefficient of the human skin of interest at, e.g., 40 GHz.

For example, a first implementation of artificial skin 100 may have a reflection coefficient of 0.71, which is constant across frequencies ranging from 1-150 GHz. In this example, the reflection coefficient is substantially equal to a first human skin reflection coefficient of interest at e.g., 40 GHz. However, at 60 GHz, this first implementation of artificial skin 100 may have a reflection coefficient substantially equal to a reflection coefficient of a second human skin of interest, but not to that of the reflection coefficient of the first human skin of interest since the reflection coefficient of human skin depends upon the frequency of the electromagnetic radiation.

The electrically conductive material 114 may have any desired reflection coefficient value, e.g. any value between 0 and 1, such as 0.2, 0.3, 0.4, 0.5, 0.6, 0.7, 0.8, etc. In some embodiments, the reflection coefficient of the electrically conductive material 114 ranges from 0.5 to 0.75, such as 0.55 to 0.69.

In some embodiments, electrically conductive material 114, optionally in combination with substrate 116, has a thickness much less than skin depth, i.e., the point at which current density reaches approximately 37% of its value at a surface of the material, for example $\lambda/10$ at an electromagnetic radiation frequency ranging from 1 to 500 GHz, such as 1 to 150 GHz, such as 70 GHz to 150 GHz, such as 18

GHz to 40 GHz. In some embodiments, the thickness of the electrically conductive material 114 optionally in combination with substrate 116 typically ranges from 200 micrometers (μm) (λ/10 at 150 GHz) or less, such as 150 nanometers (nm) or less, such as 100 nm or less, such as 10 nm or less, such as 50 Angstroms or less. Typically, thicknesses of about 100 nm are used.

Suitable materials for the electrically conductive material 114 include without limitation ultrathin metals, electrically conductive polymers and/or semiconductive materials. A suitable example of an ultrathin metal that may be used with the contrast phantom of the present disclosure includes an ultrathin silver metal. Suitable examples of electrically conductive polymers include polypyrrole, polyaniline, polyacetylene, polythiophene, polyphenylenevinylene, polyphenylene sulfide, poly p-phenylene, polyheterocyclevinylene, poly(3,4-ethylenedioxythiophene) and its derivatives.

In some embodiments, the electrically conductive polymers used with artificial skin 100 are intrinsically electrically conductive, meaning that they are electrically conductive without the addition of electrically conductive materials such as carbon or a metal, although electrically conductive polymers usually require the addition of a dopant, e.g., electrically conductive carbon doped polycarbonate which is commercially available from e.g., Azo Materials, Inc. Manchester M1 4ET, UK.

In more typical embodiments, the electrically conductive material 114 that is suitable for use with the present artificial skin includes a semiconductor material, such as semiconductive oxides, such as semiconductive metal oxides, such as tin-doped indium oxide (also known as indium tin oxide or ITO), aluminum-doped zinc oxide, indium-doped cadmium oxide, indium-doped zinc oxide, gallium-doped zinc oxide and antimony or fluorine-doped tin oxide. More typically, the semiconductive metal oxide is ITO.

One skilled in the art will appreciate that the electrical conductivity a and sheet resistance $R_s$ of an electrically conductive material 114, such as a semiconductive oxide, e.g., ITO, is determined, at least in part, by the amount of dopant, e.g., metal, doped into the semiconductive oxide. Accordingly, one implementation of an artificial skin 100 according to the present disclosure may comprise an electrically conductive material 114, which comprises tin-doped indium oxide and another implementation of artificial skin 100 according to the present disclosure may also comprise, for example, tin-doped indium oxide. Nevertheless, the conductivity a and sheet resistance $R_s$, and accordingly, reflection coefficient may vary between each implementation due to e.g., differences in the amount of tin doped into the indium oxide.

In other embodiments, an implementation of artificial skin 100 may contain a first electrically conductive material. For example, an implementation of artificial skin 100 may include an electrically conductive material 114 comprising a doped zinc oxide. Another implementation of artificial skin 100 may contain a second electrically conductive material 114 composed of comprising a doped indium oxide. In some embodiments, these different electrically conductive materials result in implementations of the present artificial skin 100 having different electrical conductivity values a, different sheet resistances $R_s$ and, accordingly, different reflection coefficient values.

Typically, the electrically conductive material 114 of the present artificial skin 100 is in the form of a coating or film. For example, ITO, which is typically a powdered mixture of indium(III) oxide ($In_2O_3$) and tin(IV) oxide ($SnO_2$), such as 90% $In_2O_3$, 10% $SnO_2$ by weight, may be deposited as a thin film or a coating onto a substrate 116.

Any desired substrate may be used e.g., glass, semiconductors, plastics, etc. In some embodiments, the substrate 116 is a flexible film such as polyethylene terephthalate (PET), polyethylene naphthalate (PEN), polyethersulfone (PES), polyetheretherketone (PEEK), polycarbonate (PC), polypropylene (PP), polyamide (PA), polyacryl (PAC), epoxy resins, phenolic resins, alicyclic polyolefins, or norbornene based thermoplastic transparent resins, or a laminate of two or more thereof.

The electrically conductive material 114, such as a semiconductive oxide, e.g., ITO, may be deposited onto a substrate 116 in any desired manner such as by planar magnetron sputtering, closed field magnetron sputtering, ion beam sputtering, rotatable magnetron sputtering or reactive thermal and electron beam evaporation. Alternatively, an electrically conductive material 114 with a known sheet resistance value, such as a semiconductive oxide, e.g., ITO, may be obtained commercially from, e.g., Sigma-Aldrich, Inc. (St. Louis, Mo.).

A reflection coefficient of the electrically conductive material 114 of the present disclosure, which may be deposited as a thin film or a coating in the thicknesses described herein, may be determined from a sheet resistance $R_s$ of the material. As used herein "sheet resistance" refers to a measure of resistance of a thin film or coating, which is substantially uniform in thickness.

For example, the magnitude of the reflection coefficient of the electrically conductive material 114 may be determined according to the following equation (1):

$$r = -1/1 + 2R_s/\eta_0 \qquad (1)$$

wherein $R_s$ is the sheet resistance of the electrically conductive material in Ω/square and $\eta_0$ is the impedance of free space, 377Ω. The negative sign in the above described equation indicates a 180° change in the phase of the reflected wave.

Further, without being limited by theory, it is believed that the type of electrically conductive material 114 of the present artificial skin 100 is, generally, not necessary for reflection coefficient determination. Instead, it is contemplated that the reflection coefficient may be determined using only the sheet resistance of the electrically conductive material.

In some embodiments, artificial skin 100 further comprises a radar absorbing layer 118. The radar absorbing layer 118 is applied on inner surface 128 of the conductive layer 120. The conductive layer 120 and the radar absorbing layer 118 may be held together with stitching, glue, or other bonding methods known in the art. Radar absorbing layer 118 is typically a rigid structure that absorbs electromagnetic energy passing from, e.g., an active millimeter wave imaging system. Suitable radar absorbing materials include electromagnetic wave absorbers using carbon ohmic resistivity with a formed polystyrol base material, such as those commercially available from e.g., TDK RF Solution, Inc. (Cedar Park, Tex.). One skilled in the art will appreciate that other materials with properties similar to those described will be suitable for use as radar absorbing material 118 of artificial skin 100.

Human Phantom

Figure 2:
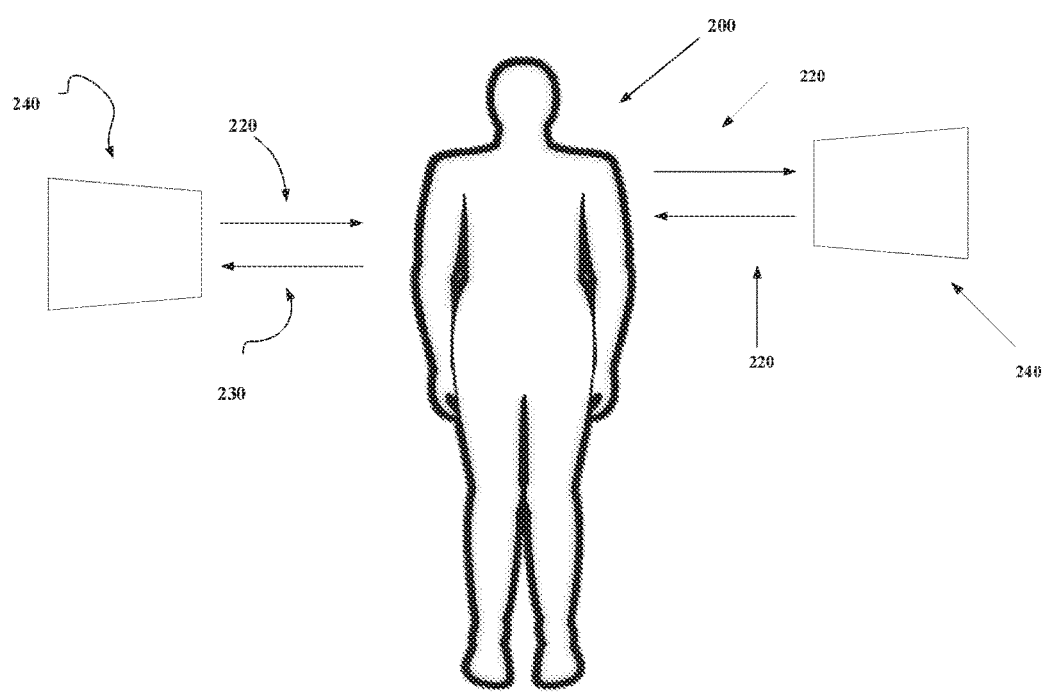
FIG. 2 depicts an implementation of a human phantom of the present disclosure as described in the detailed description.

Turning now to FIG. 2, in another implementation, artificial skin 100 is shaped to resemble a human body 200, also referred to herein as a human phantom 200. More particularly, radar absorbing material 118 of FIG. 1 is formed into a human phantom 200. The inner layer 128 of the conductive layer 120 of FIG. 1, which comprises electrically conductive material 114 and substrate 116, is attached to radar absorbing layer 118 with glue, etc. as described herein. The human phantom 200 may be in a planar or a three dimensional formation.

In some embodiments, human phantom 200 is configured to produce a reflection coefficient that is substantially equal to a reflection coefficient of a human with a normal BMI at a predetermined frequency, e.g., 1 to 500 GHz, such as 1 to 150 GHz, such as 70 GHz to 150 GHz, such as 60 to 90 GHz, such as 18 GHz to 40 GHz. In some embodiments, human phantom 200 is configured to produce a reflection coefficient that is substantially equal to a reflection coefficient of a human with an overweight BMI at a predetermined frequency. In some embodiments, human phantom 200 is configured to produce a reflection coefficient that is substantially equal to a reflection coefficient of a human with an obese BMI at a predetermined frequency.

The reflection coefficient of a human at a particular BMI of interest at a predetermined frequency may be determined, for example, by scanning a person at the desired BMI with an active millimeter wave system or the reflection coefficient may be obtained from the scientific literature. Human phantom 200 may then be configured, e.g., to produce a reflection coefficient that is substantially equal to that of the scanned person at the desired BMI by modifying the electrically conductive material 114 as described herein for the artificial skin.

In some embodiments, human phantom 200 may be configured to produce a reflection coefficient that is substantially equal to a reflection coefficient of a particular body part of a person having a normal, overweight or obese BMI, e.g., a torso, a leg, an arm or a head at a predetermined frequency, e.g., 1-500 GHz. The reflection coefficient at the predetermined frequency of the desired body part may be determined by scanning the desired body part of a person with a desired BMI at a desired frequency and then configuring electrically conductive material 114 of FIG. 1 to produce a reflection coefficient substantially equal to that of the desired body part as described herein for artificial skin.

In some embodiments, human phantom 200 may be configured to be the same height and size as that of a human of interest. In some embodiments, human phantom 200 may be configured to be of a desired average height and a desired average size as that of a human of interest. For example, the human phantom 200 may be the same average height and the same average size as that of an average man or an average woman within a desired population.

In some embodiments, human phantom 200 further includes a threat object (not shown), e.g., an explosive, a simulant thereof, a gun, a knife or a drug. The threat object (not shown) may be attached in any desired manner at any location on the human phantom 200.

In some embodiments, the human phantom 200 further comprises a foam core. In some embodiments, the inclusion of a foam core minimizes the total weight of the phantom.

Methods

In another aspect, the present disclosure is directed to a method of testing a contrast resolution sufficiency of an active millimeter wave imaging system. As used herein, "testing a contrast resolution sufficiency" refers to determining whether or not there is a perceptible difference between an object, subject and/or region of interest and a background, a second object and/or a second region of interest. The contrast resolution of an imaging system is the measure of its ability to provide the perceptible difference.

In some embodiments, the method includes imaging a human phantom as described herein with an active millimeter wave imaging system at a frequency ranging from 1-500 GHz, such as 1 to 150 GHz, such as 70 GHz to 150 GHz, such as 60 GHz to 90 GHz, such as 18 GHz to 40 GHz. Typically, the human phantom further comprises a threat object attached at any desired location on the human phantom.

FIG. 2 depicts a simplified drawing showing how a human phantom 200 may be imaged with an active millimeter wave system. In some embodiments, transceivers 240 of an active millimeter wave system are rotated around a human phantom 200 and, optionally, a threat object (not shown). The transceivers 240 can pass electromagnetic signals 220 to the human phantom 200 and the optional threat object (not shown), such as an explosive or simulant thereof. Signals 230 may then be reflected back from the human phantom 200 and the optional threat object to transceivers 240. In some embodiments, the reflected signals 230 are passed from the transceivers 240 to a processor (not shown) to form a contrast (grayscale) image of human phantom 200 and the optional threat object.

In some embodiments, the method also includes determining a presence or an absence of contrast resolution between the human phantom and the threat object, thereby testing the contrast resolution of the active millimeter wave imaging system.

In some embodiments, the method further comprises calibrating the active millimeter wave system. The calibrating step may be performed as described in the co-pending application entitled "Contrast Phantoms And Uses Thereof For an Active Millimeter Wave Imaging Systems", U.S. patent application Ser. No. 16/058,053, filed on 8 Aug. 2018, which is herein incorporated by reference in its entirety.

In some embodiments, the human phantom of the present disclosure comprises a conductive layer that includes an electrically conductive material deposited onto a substrate as described herein or an electrically conductive polymer as also herein described. In some embodiments, the electrically conductive material is a semiconductive oxide comprising a doped metal oxide, such as a tin-doped indium oxide, an aluminum-doped zinc oxide, an indium-doped cadmium oxide, an indium-doped zinc oxide or a gallium doped zinc oxide. Typically, the deposited semiconductive oxide is a tin-doped indium oxide.

In some embodiments, the reflection coefficient of the present human phantom used with the present method is substantially equal to a reflection coefficient of a human skin with a normal body mass index, an overweight body mass index or an obese body mass index as herein described. Typically, however, the reflection coefficient of the human phantom is substantially equal to a reflection coefficient of a human skin with a normal body mass index at a predetermined frequency.

We claim:

1. An artificial skin comprising:
a radar absorbing layer;
a conductive layer comprising at least one electrically conductive material selected from the group consisting of
a semiconductive oxide deposited onto a substrate and an electrically conductive polymer,
wherein the substrate is in contact with the radar absorbing layer, and
wherein the artificial skin has a reflection coefficient substantially equal to a human skin reflection coefficient, the human skin reflection coefficient being determined at an electromagnetic radiation frequency ranging from 1-500 GHz.

2. The artificial skin of claim 1,
wherein the conductive layer comprises the deposited semiconductive oxide.

3. The artificial skin of claim 2,
wherein the deposited semiconductive oxide comprises a doped metal oxide.

4. The artificial skin of claim 2, wherein the deposited semiconductive oxide is selected from the group consisting of
a tin-doped indium oxide,
an aluminum-doped zinc oxide,
an indium-doped cadmium oxide,
an indium-doped zinc oxide and
a gallium doped zinc oxide.

5. The artificial skin of claim 2,
wherein the deposited semiconductive oxide is a tin-doped indium oxide.

6. The artificial skin of claim 1,
wherein the human skin reflection coefficient is determined from a skin of a human with a normal body mass index.

7. The artificial skin of claim 1,
wherein the human skin reflection coefficient is determined from a skin of a human with an overweight body mass index.

8. The artificial skin of claim 1,
wherein the human skin reflection coefficient is determined from a skin of a human with an obese body mass index.

9. The artificial skin of claim 1,
wherein the substrate is polyethylene terephthalate.

10. A human phantom comprising:
a surface comprising a radar absorbing layer; and
a conductive layer comprising an electrically conductive material, wherein the electrically conductive material is selected from the group consisting of
a semiconductive oxide deposited onto a substrate and an electrically conductive polymer, wherein the substrate is in contact with the radar absorbing layer, and
wherein the conductive layer has a reflection coefficient substantially equal to a human skin reflection coefficient, the human skin reflection coefficient being determined at an electromagnetic radiation frequency in a range from 1-500 GHz.

11. The human phantom of claim 10,
wherein a threat object is attached to the human phantom.

12. The human phantom of claim 11,
wherein the threat object is an explosive.

13. The human phantom of claim 10,
wherein the electrically conductive material is the deposited semiconductor.

14. The human phantom of claim 13,
wherein the deposited semiconductor is a tin-doped indium oxide.

15. The human phantom of claim 10,
wherein the electromagnetic radiation frequency ranges from 60-90 GHz.

16. A method of testing a contrast resolution sufficiency of an active millimeter wave imaging system comprising:
imaging a human phantom comprising a threat object with an active millimeter wave imaging system, wherein the human phantom comprises:
a surface comprising a radar absorbing layer;
a conductive layer comprising an electrically conductive material deposited onto a substrate, wherein the substrate is in contact with the surface comprising the radar absorbing layer, wherein the electrically conductive material is selected from the group consisting of a semiconductive oxide and an electrically conductive polymer, and
wherein the conductive layer has a reflection coefficient substantially equal to a reflection coefficient of human skin, the reflection coefficient of human skin being determined at an electromagnetic radiation frequency ranging from 1-500 GHz, and
determining a presence or absence of contrast resolution between the human phantom and the threat object, thereby testing the contrast resolution sufficiency of the active millimeter wave imaging system.

17. The method of claim 16,
wherein the threat object is an explosive.

18. The method of claim 16,
wherein the electrically conductive layer is the deposited semiconductive oxide.

19. The method of claim 16,
wherein the reflection coefficient of the human phantom is substantially equal to a reflection coefficient of a human skin with an overweight body mass index.

20. The method of claim 16,
wherein the reflection coefficient of the human phantom is substantially equal to a reflection coefficient of a human skin with a normal body mass index.

21. The method of claim 16,
wherein the reflection coefficient of the human skin is determined at an electromagnetic radiation frequency ranging from 60-90 GHz.

* * * * *